(12) United States Patent
Stripf et al.

(10) Patent No.: US 7,657,403 B2
(45) Date of Patent: Feb. 2, 2010

(54) METHOD FOR REDUCING DIGITAL DATA IN AN EMAT PIG

(75) Inventors: Helmut Stripf, Eggenstein-Leopoldshafen (DE); Matthias Balzer, Karlsruhe (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 367 days.

(21) Appl. No.: 11/815,592

(22) PCT Filed: Jan. 19, 2006

(86) PCT No.: PCT/EP2006/000425

§ 371 (c)(1),
(2), (4) Date: Aug. 6, 2007

(87) PCT Pub. No.: WO2006/081946

PCT Pub. Date: Aug. 10, 2006

(65) Prior Publication Data

US 2008/0215257 A1    Sep. 4, 2008

(30) Foreign Application Priority Data

Feb. 5, 2005   (DE) ........................ 10 2005 005 386

(51) Int. Cl.
*H04B 15/00* (2006.01)
*G01N 9/24* (2006.01)
*G01V 1/00* (2006.01)

(52) U.S. Cl. ............................ 702/190; 73/602; 367/35

(58) Field of Classification Search .................. 702/39, 702/190; 367/28, 35; 73/597, 602
See application file for complete search history.

(56) References Cited

U.S. PATENT DOCUMENTS

| 5,635,645 A | 6/1997 | Ottes et al. |
| 7,234,355 B2 * | 6/2007 | Dewangan et al. ............ 73/622 |
| 2005/0072237 A1 * | 4/2005 | Paige et al. .................. 73/623 |

FOREIGN PATENT DOCUMENTS

DE    40 40 190    6/1992

(Continued)

OTHER PUBLICATIONS

V. Deutsch et al.: "3.4.3.6 Rechnergestützte Fehlerbeschreibung", Ultraschallpruefung: Grundlagen und Industrielle Anwendungen, 1997, pp. 133-141, XP-002278716, p. 137, paragraph 2—p. 140, paragraph 1, figures 3.121-3.123.

(Continued)

*Primary Examiner*—Bryan Bui
(74) *Attorney, Agent, or Firm*—Darby and Darby

(57) ABSTRACT

A method for reducing digital data of an electro magnetic acoustic transducer pig that travels through a pipeline so as to detect defects by measuring an analog ultrasonic echo includes determining a size of a defect and determining a background noise at the defect. The size of the defect is determined by selecting peak values of the digital data based on a plurality of amplitude/transit time vectors indicating maxima of an ultrasound envelope, each vector being determined by three amplitude/transit time pairs. The ultrasound envelope is generated by determining a width of a respective vector ultrasound envelope for each vector. The background noise at the defect is determined by summing peak values of the digital data in time intervals so as to form an interval-specific summation value.

8 Claims, 3 Drawing Sheets

FOREIGN PATENT DOCUMENTS

| | | |
|---|---|---|
| DE | 4141123 | 3/1993 |
| DE | 4409999 | 12/1994 |
| DE | 10353132 | 6/2005 |
| GB | 2 380 794 | 4/2003 |

OTHER PUBLICATIONS

O. A. Barbian et al.: "Signalanhebung durch Entstörung von Laufzeit-Messwerten aus Ultraschallpruefungen von ferritischen und austenitischen Werkstoffen—AOLK (Amplitude-Laufzeit-Ortskurve)—Teil 1" [Signal enhancement by noise elimination of transit time measurement data by ultrasonic inspection of ferritic and austenitic materials—ALOK—part 1], Materials Testing West Germany, vol. 23, No. 11, Nov. 11, 1981, pp. 379-383, XP009067220.

M. Balzer et al. "Online data reduction with a dsp-fpga multiprocessor system", Digital Signal Processing, 2002, DSP 2002, 2002 14th International Conference on Piscataway, NJ, USA, IEEE, US, vol. 2, Jul. 2002, pp. 819-822, XP010599978.

* cited by examiner

METHOD FOR REDUCING DIGITAL DATA IN AN EMAT PIG

CROSS REFERENCE TO PRIOR APPLICATION

This is a U.S. national phase application under 35 U.S.C. §371 of International Patent Application No. PCT/EP2006/000425, filed Jan. 19, 2006, and claims benefit of German Patent Application No. 10 2005 005 386.6, filed Feb. 5, 2005, which is incorporated by reference herein. The International Application was published in German on Aug. 10, 2006 as WO 2006/081946 A1 under PCT Article 21(2).

The present invention relates to a method for reducing digital data which from digital data obtained from measured values in an Electro Magnetic Acoustic Transducer (EMAT) pig, which detects cracks, corrosion, or other abnormalities/damage of/to a pipe wall, and compresses the same by means of computing modules.

BACKGROUND

In order to inspect pipelines, especially for the transport of oil or gas, it is known to use inspection pigs which have specifically sensitive sensors arranged on their outer shell around the periphery thereof. Using these sensors, the condition of the pipeline is sensed, and can thereby be verified. Sensors that are suitable for this purpose are based on different physical principles. Known sensors include, for example, piezoelectric, electro-acoustic, magnetic sensors, and the EMAT sensors mentioned above.

The measured data obtained by the sensors is converted into electrical analog signals and digitized in an analog-to-digital converter for further processing/use. During a run through a long oil/gas pipeline, tremendous amounts of data are generated. During such a run, such a pig is not connected to the outside world. Therefore, the generated data must be stored in a form that allows the wall condition to be reconstructed outside the pipeline after the run, allowing abnormalities/damage/defects of/to the pipe wall to be located and reliably quantified. In the case of direct (1:1) data storage, even modern memories will overflow. Therefore, the digital data generated from the analog values must be reduced/compressed in a way that will ensure the reconstruction stipulated hereinabove. Qualitatively, this means that there is no need to store data of inconspicuous/sound areas of the pipe wall. Thus, in the detection of damage in walls of long/very long pipelines, data reduction methods are used to extract the essential features of a signal associated with a defect in the pipe wall, and to represent said features as accurately as possible with a minimum number of bits to thereby reduce/minimize the amount of data to be stored.

The amplitude-transit time-position curve (ALOK) method (O. A. Barbian, B. Grohs, R. Licht, "Signalanhebung durch Entstörung von Laufzeit-Messwerten aus Ultraschallprüfungen von ferritischen und austenitischen Werkstoffen—ALOK", Teil 1. Materialprüf. 23 (1981) 379-383] [Signal enhancement by suppressing noise in transit time measurement data from ultrasonic inspection of ferritic and austenitic materials—ALOK", part 1, Materials Testing, Vol. 23, (1981), pp. 379-383] selects the peaks of the ultrasound envelope. This makes it possible to achieve a high reduction factor. However, essential information is lost from the signal during reduction. For example, the stored data does not provide any information about the shape of the ultrasonic reflection or about the background in the region of the selected vectors. However, this information is very important for determining the structure and size of the defect. Moreover, peak structures in the noise are selected as being worthy to be stored, thus worsening the reduction factor.

German Patent DE 4040 190 describes a method in which the amplitude maximum and the time value are stored when a predetermined threshold is no longer met. However, the method does not analyze the width and characteristic of the envelope. In addition, the method requires an ultrasonic signal that is smoothed by a low-pass filter.

In EMAT technology, an EMAT probe including an EMAT transmitter and an EMAT receiver produces an ultrasonic wave train (US wave train) in the pipe/pipeline wall by electrical/magnetic forces, said ultrasonic wave train having a predetermined number of wavelengths, preferably 5-10 wavelengths. This wave train propagates through the pipeline wall and is reflected at interfaces. The reflected US wave is detected by the EMAT receiver and converted back into a proportional electrical signal (see GB 2 380 794 A). The transmitter can send single pulses and waves of different shape and frequency, depending on the waveform generator incorporated therein. Sensors typically used have transmitter frequencies between about 400 kHz and about 2 MHz. The data of the electromagnetic sensors are recorded at a resolution of 12-16 bits and at a sampling rate of, for example, 20 MHz, using analog-to-digital (AD) converters. For an inspection pig having 50 sensors which are at least partially operated in multiplex mode, and an inspection speed of 1 m/sec, about 200 TB of data is typically generated over a pipeline length of 500 km. This data volume must be stored in the traveling pig during the inspection run, because there is no connection to the outside while the pig is moving.

Depending on the microstructure of the steel, the surface structure and the coating of the pipeline, the signal detected by the receiver can vary very strongly even if the steel is free of defects. This leads to fluctuations in the signal background. However, the echo amplitude reflected by a crack in relation to the background is very important for determining the size of the crack.

In order to limit the volume of data to storable amounts and to achieve an economic range for the pig, it is mandatory to perform data reduction.

SUMMARY

It is an aspect of the present invention to achieve higher reduction factors by developing a special reduction method which, based on the knowledge of the structure of the data and its weighting for offline analysis of defects, is adapted to the requirements of the signal analysis.

In an embodiment, the present invention provides a method for reducing digital data of an electro magnetic acoustic transducer pig that travels through a pipeline so as to detect defects by measuring an analog ultrasonic echo having an ultrasonic frequency. The method includes:

determining a size of a defect by selecting peak values of the digital data based on a plurality of amplitude/transit time vectors indicating maxima of an ultrasound envelope, each vector being determined by three amplitude/transit time pairs, the selecting peak values being performed by:

generating the ultrasound envelope by determining a width of a respective vector ultrasound envelope for each vector of the vectors by determining, from peak amplitudes in an immediate vicinity of each of the vectors, minima around each vector that are below a predetermined threshold;

storing a respective time distance between the minima and a time value of each vector;

if none of the peak amplitudes between a first and a second of the vectors is less than the predetermined threshold, selecting the peak amplitude having a minimum amplitude value as the minimum following the first vector and the minimum preceding the second vector, the second vector following the first vector;

excluding vector ultrasound envelopes having a width that is less than an envelope threshold value; and excluding vector ultrasound envelopes having a shape characteristic not satisfying a predetermined characteristic, the shape characteristic of a respective vector ultrasound envelope being determined by a ratio of a time difference between the time value of the respective vector and the preceding minimum to a time difference between the time value of the respective vector and the following minimum, the shape characteristic not satisfying the predetermined characteristic when the ratio lies outside a predetermined range; and determining a background noise at the defect by:

dividing the time domain of the ultrasonic echo into time intervals having at least the duration of 4 wavelengths of the ultrasonic frequency and have parameterized starting and length values;

summing the peak values of the digital data in the time intervals so as to form an interval-specific summation value; and dividing the summation value by the number of peaks in the interval so as to provide a mean peak value of the interval.

BRIEF DESCRIPTION OF THE DRAWINGS

The drawings include FIGS. 1 through 5, of which

DETAILED DESCRIPTION

The data reduction method is intended particularly for use in an EMAT pig which detects cracks, corrosion, and other abnormalities/damage of/to a pipe wall as it travels through a pipe to be inspected. During the measurement run, the analog measurement signals from the electromagnetic sensors are digitized, compressed by computing modules, and stored in a data storage system which is located in and moves together with the pig. The method for reducing/compressing data is divided into three basic steps/methods for processing the generated data:

pre-compression feature extraction, and compression.

The EMAT sensor installed in the pig includes at least one transmitter/receiver unit. The sensor generates an ultrasonic wave train of a selectable type of wave and a selectable frequency in the range from about 400 kHz to about 2 MHz and directs said ultrasonic wave train toward the pipe wall. The echo of the ultrasonic wave train coming from the pipe wall is detected by the at least one EMAT receiver. The echo is converted back into an electrical analog signal, digitized by an analog-to-digital (AD) converter, and then rectified (see FIG. 1).

The objective of improving the data reduction is achieved by the method steps described in claim 1, which are divided into two method groups, namely:

determination of the size of a defect, and determination of the signal background in the vicinity of a defect.

Figure 3:
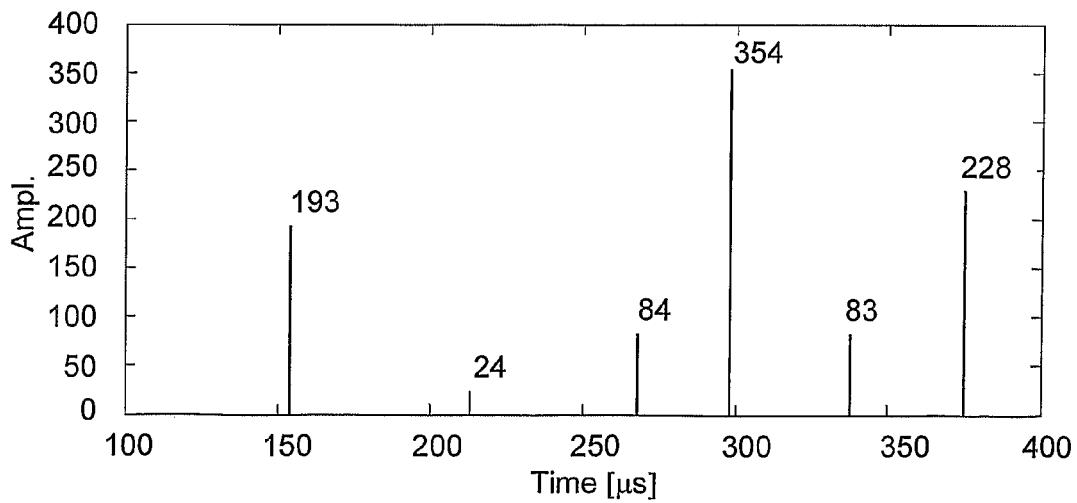
FIG. 3 is a signal diagram illustrating the ultrasonic signal after the selection of the peak maxima in a vector representation.

Size Determination:

The method steps for size determination are based on an algorithm for selecting peak values, said algorithm yielding amplitude/transit time pairs, i.e., vectors, which indicate the maxima of the ultrasound envelope (see FIG. 3). The transit time pairs will herein be referred to as "vectors". Below a parameterized threshold, the vectors are selected, thus extracting the noise.

The generation of the envelope is accomplished in such a way that for each selected vector, the width of the ultrasound envelope is additionally determined. To this end, the minima around each vector that are below the predetermined threshold are determined from the peak amplitudes in the immediate vicinity of the vector. The time distance between the minima and the time value of the vector is stored. The envelope is reconstructed offline at a later time with sufficient accuracy by interpolation between the individual time values and vectors. If the peak amplitude between two vectors is not less than the threshold, the peak with the minimum amplitude values is determined as the minimum, which is the minimum following the first vector and the minimum preceding the following vector (see FIG. 4).

The envelope vectors whose width is less than a threshold value, the so-called "envelope width", are excluded. Envelope vectors whose shape cannot be correlated with a predetermined characteristic, the so-called "envelope shape", are also excluded. Thus, the envelope vector is determined by the amplitude and the time value/time of occurrence of the respective maximum, and by the envelope width and the envelope shape. The characteristic of the envelope shape is determined by the ratio of the time difference between the time value of the maximum and the preceding peak minimum to the time difference between the time value of the maximum and the following peak minimum. If the parameterizable ratio is, for example, larger than the value 2 or smaller than 0.5, then the envelope shape does not satisfy the predetermined characteristic. The envelope vector will then be excluded.

Each envelope vector is determined by three amplitude/transit time pairs, namely by the maximum, the preceding peak minimum, and the following peak minimum.

Via the generation of the envelope, in combination with the envelope width and the envelope shape, feature extraction is performed on the pre-compressed/vectorized ultrasonic signal in order to decide whether the ultrasonic signal contains any informative features and whether it would therefore have to be stored.

Signal Background:

Since, as has been explained earlier, the signal background leads to fluctuations in the signal, the determination of the signal background is very important for determining the size of a crack in relation to the background. Here, the time domain of the ultrasonic echo is therefore divided into time intervals which are arbitrary, but have at least the duration of 4 adjacent wavelengths of the ultrasonic frequency used and have parameterized starting and length values. In these time intervals, the amplitudes of the peaks are summed to form an interval-specific summation value which is then divided by the number of peaks, thereby taking the mean thereof. For size determination purposes, each mean value is determined at the associated defect and stored. The background values adjacent to the defect in the azimuthal and radial directions are used offline to determine the size of a defect.

Data compression is performed on the selected features without losing important information. In the process, the data is encoded without losing information about the defect. The time values are stored at different resolutions, depending on the importance, thereby achieving a higher compression factor. The time value of the maximum is important for the position resolution of a detected defect, but the time values of the envelope width are of secondary importance. By encoding at different time resolutions, a higher compression factor is achieved.

Figure 2:
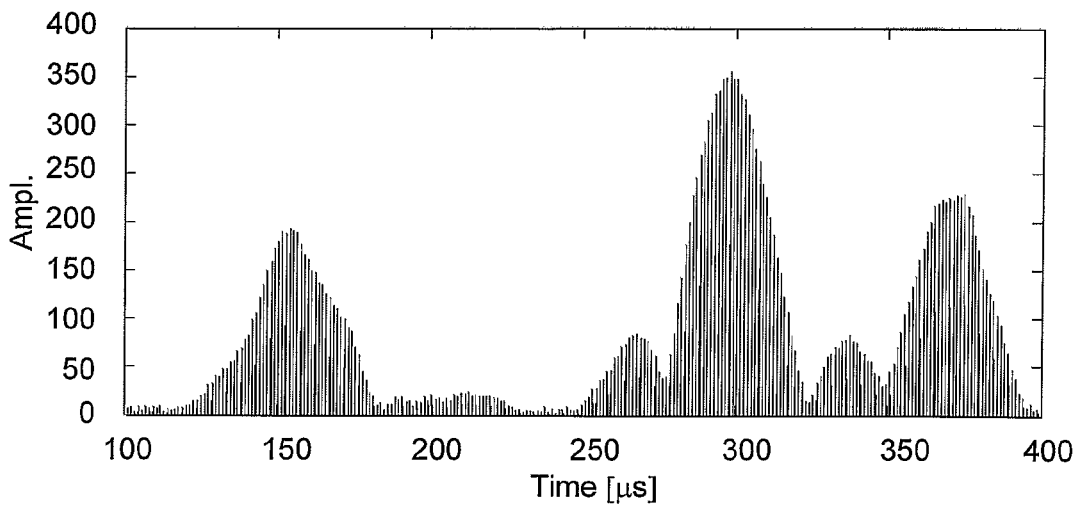
FIG. 2 shows the peaks of the ultrasonic signal.

In an embodiment, the determination of the maximum is carried out in a defined time interval having at least the magnitude of half a wavelength (sampling theory) (see also FIG. 2).

Compared to conventional methods, the present method increases fidelity of reproduction without increasing or significantly increasing the amount of data to be stored. After the inspection run of the EMAT pig, using the present method, the ultrasound envelope can be reconstructed without loss of information, or at least without significant loss of information, from the data stored in reduced form. Via the method group of size determination, the method analyzes the width of the envelope, which is a powerful feature. Via the method group of determining the signal background, the size determination is evaluated in terms of its quality.

Figure 1:
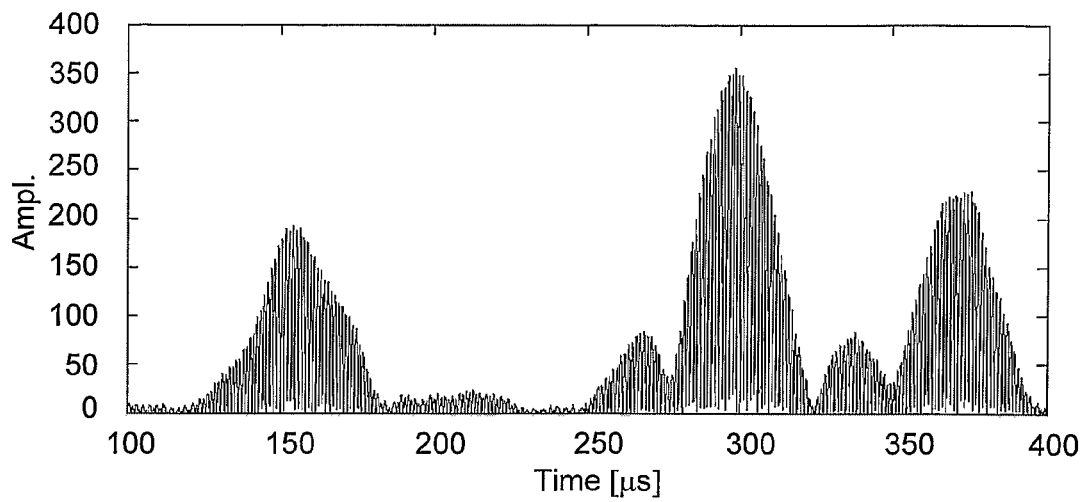
FIG. 1 shows the digitized and smoothed ultrasonic signal.

FIGS. 1 through 4 have already been made reference to in the above description. In FIG. 1, the significant echo of a crack is shown at about 150 μs. The transmission signals of the adjacent transmitters can be seen at about 300 μs and at about 370 s. The sensor arrangement is described in GB 2 380 794 A (see in particular FIG. 3 and the passages of the description on page 6, line 26, through page 7, line 18, therein).

Figure 4:
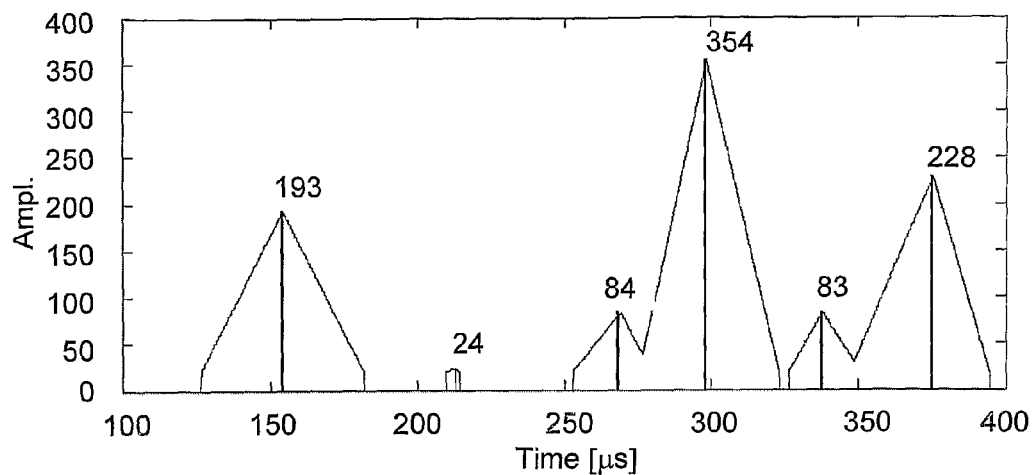
FIG. 4 is an envelope representation of the ultrasonic signal.

Compared to FIG. 3, the envelope-vector representation of the ultrasonic signal in FIG. 4 illustrates the ultrasound envelope better than the pure vector representation.

Figure 5:
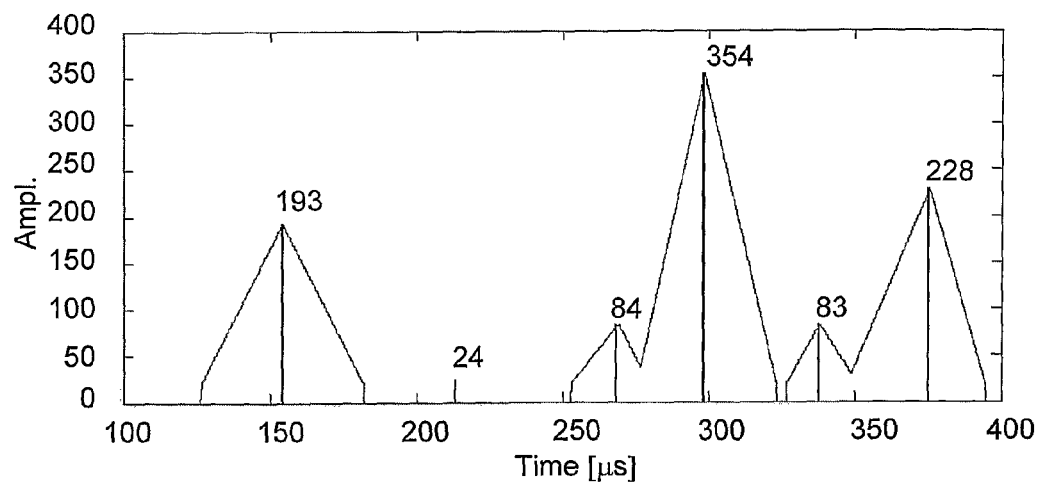
FIG. 5 shows the envelope representation with the vectors excluded.

In FIG. 5, the envelope-vector representation is shown with the vectors (denoted by 34) excluded whose envelope widths are less than a minimum width.

Figure 6:
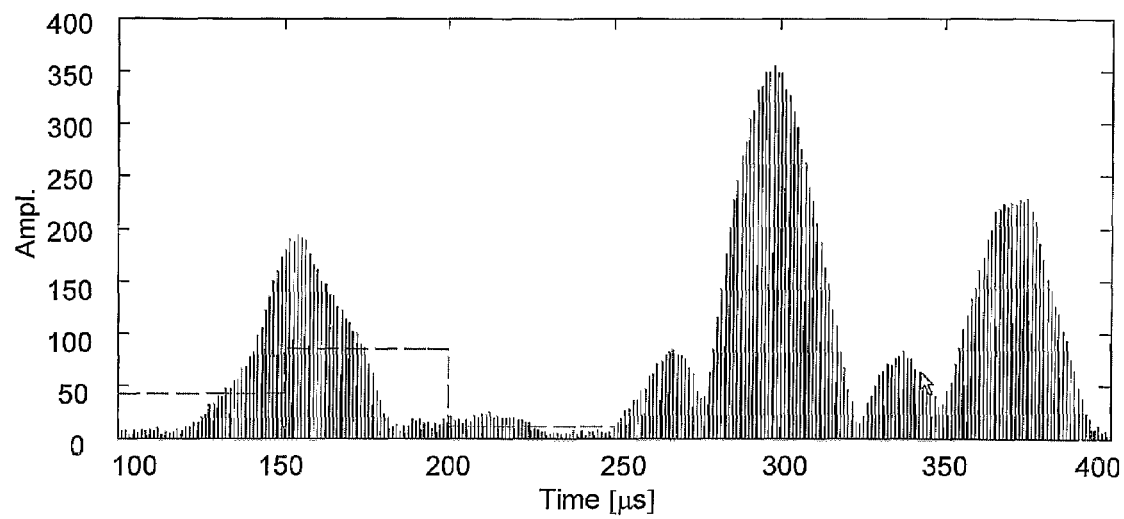
FIG. 6 shows the peaks and their mean values.

In FIG. 6, the representation of the peaks and the mean values of the peaks is shown in three intervals: 100 μs-150 μs, 150 μs-200 μs, 200 μs-250 μs.

Figure 7:
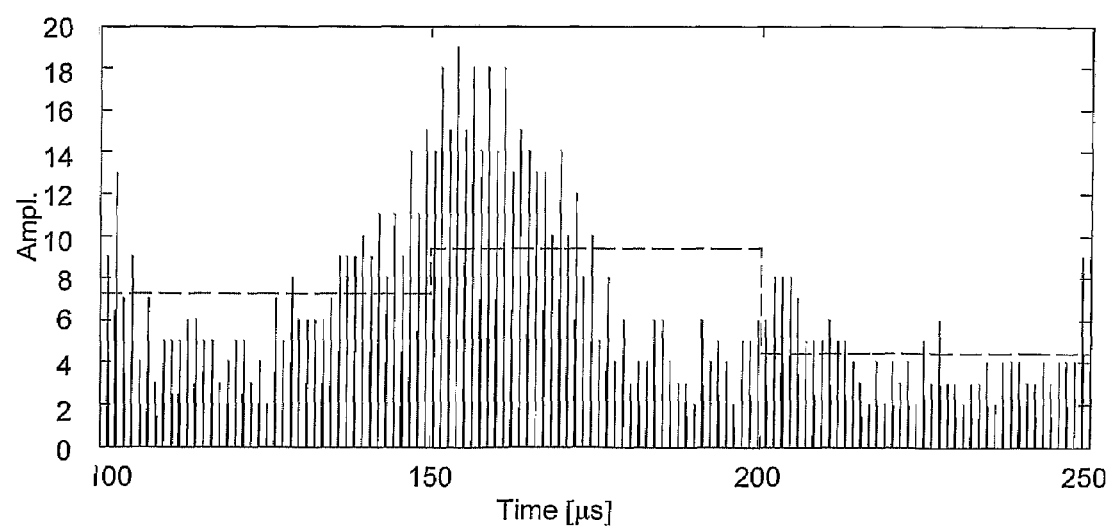
FIG. 7 shows the peaks and the mean values without any defect.

For further illustration, FIG. 7 shows, on a different/enlarged scale, both vertically and horizontally, the representation of the peaks and the mean values of the peaks of an ultrasound echo without any defect in three intervals: 100 μs-150 μs, 150 μs-200 μs, 200 μs -250 μs.

The present invention is not limited to the exemplary embodiments described herein.

What is claimed is:

1. A method for reducing digital data of an electro magnetic acoustic transducer pig that travels through a pipeline so as to detect defects by measuring an analog ultrasonic echo having an ultrasonic frequency, the method comprising:
determining a size of a defect by selecting peak values of the digital data based on a plurality of amplitude/transit time vectors indicating maxima of an ultrasound envelope, each vector being determined by three amplitude/transit time pairs, the selecting peak values being performed by:
generating the ultrasound envelope by determining a width of a respective vector ultrasound envelope for each vector of the vectors by determining, from peak amplitudes in an immediate vicinity of each of the vectors, minima around each vector that are below a predetermined threshold;
storing a respective time distance between the minima and a time value of each vector;
if none of the peak amplitudes between a first and a second of the vectors is less than the predetermined threshold, selecting the peak amplitude having a minimum amplitude value as the minimum following the first vector and the minimum preceding the second vector, the second vector following the first vector;
excluding vector ultrasound envelopes having a width that is less than an envelope threshold value; and
excluding vector ultrasound envelopes having a shape characteristic not satisfying a predetermined characteristic, the shape characteristic of a respective vector ultrasound envelope being determined by a ratio of a time difference between the time value of the respective vector and the preceding minimum to a time difference between the time value of the respective vector and the following minimum, the shape characteristic not satisfying the predetermined characteristic when the ratio lies outside a predetermined range; and
determining a background noise at the defect by:
dividing the time domain of the ultrasonic echo into time intervals having at least the duration of 4 wavelengths of the ultrasonic frequency and have parameterized starting and length values;
summing the peak values of the digital data in the time intervals so as to form an interval-specific summation value; and
dividing the summation value by the number of peaks in the interval so as to provide a mean peak value of the interval.

2. The method as recited in claim 1 wherein the defect includes at least one of a crack, a corrosion area and a damage area.

3. The method as recited in claim 1 wherein the selecting peak values and determining the signal background noise are performed so as to enable the defect to be located and evaluated in terms of its quality upon a reading out of the data after a pig run.

4. The method as recited in claim 1 further comprising storing the mean peak value associated with the defect.

5. The method as recited in claim 1 further comprising storing the time values of the vectors at different respective resolutions so as to achieve enhanced compression.

6. The method as recited in claim 1 further comprising determining a respective maximum of the analog ultrasonic echo in defined time intervals having at least a magnitude of half a wavelength of the ultrasonic echo so as to provide the digital data.

7. The method as recited in claim 1 further comprising storing non-excluded vector ultrasound envelopes.

8. The method as recited in claim 1 further comprising storing the mean peak value of the interval.

* * * * *